United States Patent [19]

Lee et al.

[11] 4,152,315

[45] May 1, 1979

[54] BIS(POLYORGANOSILOXANYL)AMINES AND THEIR USE

[75] Inventors: Chi-Long Lee; Myron T. Maxson, both of Midland, Mich.

[73] Assignee: Dow Corning Corporation, Midland, Mich.

[21] Appl. No.: 904,046

[22] Filed: May 8, 1978

[51] Int. Cl.$^2$ .................. C08L 83/04; C07F 7/02
[52] U.S. Cl. .................. 260/37 SB; 260/448.2 N
[58] Field of Search .................. 260/37 SB, 448.2 N

[56] References Cited

U.S. PATENT DOCUMENTS

| | | | |
|---|---|---|---|
| 3,024,126 | 3/1962 | Brown | 260/37 SB |
| 3,122,516 | 2/1964 | Polmanteer | 260/37 SB |
| 3,243,404 | 3/1966 | Martellock | 260/46.5 E |
| 3,624,023 | 11/1971 | Hartlage | 260/37 SB |
| 3,927,057 | 12/1975 | Takamizawa et al. | 260/448.2 E |
| 4,008,198 | 2/1977 | Krohberger et al. | 260/46.5 G |
| 4,116,919 | 9/1978 | Elias et al. | 260/37 SB |

*Primary Examiner*—Lewis T. Jacobs
*Attorney, Agent, or Firm*—Roger H. Borrousch

[57] ABSTRACT

Vinyl and allyl containing bis(polydimethylsiloxanyl)amine compounds are useful as a treating agent for pinely divided silica when used in conjunction with conventional silazanes. The in situ filler treatment using the amine compounds and silazanes allows the production of easily extrudable compositions which cure to silicone elastomers with unique property profiles.

10 Claims, No Drawings

BIS(POLYORGANOSILOXANYL)AMINES AND THEIR USE

BACKGROUND OF THE INVENTION

1. Field of the Invention

This invention relates to a short chain linear bis(polyorganosiloxanyl)amine, its use in treating finely divided silica fillers and elastomeric compositions and cured products made therefrom.

2. Description of the Prior Art

In the silicone elastomer art, the treatment of reinforcing silica fillers is now well known as a means of retarding or preventing reaction between the surface of reinforcing filler and silicone polymer. This interaction produces what is termed "structuring" or "crepe aging" and results in a loss of workability of such mixtures. U.S. Pat. No. 3,243,404 of Martellock describes silicone compositions containing silicon-nitrogen process aids, the silicon-nitrogen material being a member selected from the class consisting of:

(a) a silyl amine having the formula

$(R^*)_b Si(N(R^*)_2)_{4-b}$ (b) a silicon-nitrogen compound having the formula

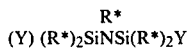

$(Y)(R^*)_2 SiNSi(R^*)_2 Y$
 with $R^*$ above and (c) a silicon-nitrogen polymer comprising (1) from 3 to 100 mole percent of units selected from the class consisting of

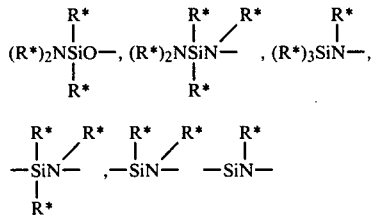

(2) from 0 to 97 mole percent units represented by the formula

$(R^*)_c SiO_{(4-c/2)}$ wherein $R^*$ is a monovalent hydrocarbon radical or halogenated monovalent hydrocarbon radical as further defined in the patent.

U.S. Pat. No. 3,024,126 of Brown teaches a method of solvent treatment of reinforcing silicas with hydroxyl or alkoxy silanes and siloxanes in contact with certain amine, quaternary ammonium, and organometallic compounds. The amine is further defined as ammonia or any amino compound with a basic dissociation constant in dilute solution in water of at least $10^{-7}$ at 25° C., thus the amino compound can be ammonia, a primary amine, a secondary amine, a tertiary amine, or any combination.

In U.S. Pat. No. 3,927,057 Takamizawa et al. describe an efficient method of making organosilylamines. The organosilylamines are obtained from reacting triorganohalosilanes of the general formula $R_3^*SiX$ with a nitrogen-containing compound selected from the group consisting of ammonia and amines represented by the general formula $R_2^*NH$, wherein $R^*$ is further defined in the patent.

It has been found that specific combinations of diorganopolysiloxane, reinforcing silica, and process aids or treating agents may impart particular properties to the cured elastomers. In U.S. Pat. No. 4,008,198 Krohberger et al. have taught that a highly viscous diorganopolysiloxane mixed with a reinforcing silicon dioxide filler, a hexaorganodisilazane, and a nitrogen containing compound having at least one triorganosilyl group in which at least one nitrogen atom is linked either directly to a silicon atom or via an oxygen atom, but no more than one triorganosilyl group is linked directly to a nitrogen atom and no more than one condensable group is linked to a silicon atom yields a composition which may be cured by the addition of a curing agent to form highly transparent or optically clear elastomers. Included as an example of many such nitrogen containing compounds taught are aminorganosiloxanes such as those corresponding to the general formula $R_3^*Si(OSiR_2^*)pNR_2^*$ where $R^*$ is as further defined in the patent and p is a whole number having a value of from 1 to 20. In U.S. Pat. No. 3,122,516 Polmanteer taught that a great improvement in the high temperature strength of silicon rubber can be obtained by incorporating certain modified silica fillers into otherwise conventional silicone rubber formulations. These fillers were made up of $SiO_2$ units or combinations of $SiO_2$ units and $R^*SiO_{1.5}$ units and had their surface saturated with $R_n^*SiO_{(4-n/2)}$ units (I) and $R_x^*(CH_2=CH)SiO_{(3-x/2)}$ units (II) such that (I) units were present in amounts of 4 to 29.9 per 100 filler units and (II) units were present in amounts of 0.1 to 2 per 100 filler units wherein the total of (I) and (II) units was from 6 to 30 units per 100 filler units. $R^*$ is a monovalent hydrocarbon radical or halogenated monovalent hydrocarbon radical as further defined in the patent.

SUMMARY OF THE INVENTION

A bis(polyorganosiloxanyl)amine of the general formula

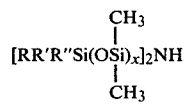

$$[RR'R''Si(OSi)_x \underset{CH_3}{\overset{CH_3}{|}}]_2 NH$$

which is useful in conjunction with silazane of the general formula $(G_3Si)_2NH$ provides a treating agent for finely divided silica. The treated filler can be used to make curable silicone elastomer compositions which cure to products with unique property profiles. These treated silicas can be used to produce low viscosity compositions useful in low pressure molding systems while still maintaining usefully high values of durometer and modulus.

The bis(polyorganosiloxanyl)amine of this invention allows the production of useful products wherein less of the treating agent is used thereby producing the finished product at a lower cost.

DESCRIPTION OF THE INVENTION

This invention relates to a bis(polyorganosiloxanyl)amine of the formula $$[RR'R''Si(OSi)_x]_2NH \quad \text{with two } CH_3 \text{ groups on central N} \quad (i)$$

where R is methyl, ethyl, or phenyl; R' is methyl or ethyl; R" is vinyl or allyl; and x is an integer of from 2 to 12 inclusive. This invention also relates to the use of the above bis(polyorganosiloxanyl)amine in conjunction with a silazane of the formula $$(G_3Si)_2NH \qquad (ii)$$

wherein each G is selected from a group consisting of lower alkyl, phenyl, and 2-(perfluoroalkyl)ethyl radicals in which each perfluoroalkyl radical has from 1 to 4 inclusive carbon atoms, as a treating agent for finely divided silica which is useful as a filler in curable silicone elastomer compositions.

The treating agent described above can be used to treat finely divided silica. This treated silica can be used to reinforce polydiorganosiloxane fluids which can subsequently be compounded with organohydrogensiloxane cross-linkers and platinum containing catalysts to yield cured silicone elastomers with desirable physical properties. These physical properties are obtained through the use of the unique combination of ingredients in the treating agent used to treat the silica filler rather than through the use of larger amounts of filler. The use of large amounts of available silica fillers is not a satisfactory method of improving physical properties of low viscosity composition because the viscosity of the uncured mixture increases to levels which require stronger, more expensive molds and stronger, more expensive means of forcing the mixture into a mold for shaping and curing.

Through the use of the treating agent of this invention, it is possible to produce uncured compositions suitable for use in low pressure molding systems for silicone elastomers. These systems require an uncured composition capable of being pumped or pushed by air pressure in the range of about 0.6 to 0.7 MPa, rather than being forced into a mold by a ram or extrusion screw such as used in conventional molding processes for elastomers based on gums.

The finely divided silica used in the preparation of the present invention can be any of the available reinforcing silica fillers with a surface area of at least 50 square meters per gram. These reinforcing silica fillers are well known in the art and can be obtained commercially. They are most often produced by burning silanes, for example silicon tetrachloride. The preferred silicas have surface areas from 200 to 400 square meters per gram. The surface of the silica normally contains Si—OH groups as well as Si—O—Si groups. An amount of water may also be absorbed on the surface.

The bis(polyorganosiloxanyl)amine of formula (i) can be produced by reacting a corresponding chlorosilane of the formula $$RR'R''Si(OSi)_xCl \quad \text{with two } CH_3 \text{ groups}$$

with ammonia to yield the bis(polyorganosiloxanyl)amine. This method is well known in the art as shown by C. Eaborn, "Organosilicon Compounds" Butterworths Scientific Publications, London, 1960, Chapter 11, page 339 to 350.

A number of methods are known in the art for the preparation of the monochlorosiloxanes used in the preparation of the bis(polyorganosiloxanyl)amines of this invention. One method is described by Brown and Hyde in U.S. Pat. No. 3,162,662 wherein a monochlorosilane can be reacted with cyclotrisiloxane in the presence of acetonitrile and N,N-dimethylacetamide. For this invention the monochlorosilane would be RR'R"SiCl where R is methyl, ethyl, or phenyl; R' is methyl or ethyl; and R" is vinyl or allyl. The preferred monochlorosilane would be dimethylvinylchlorosilane. For this invention the cyclotrisiloxane would be hexamethylcyclotrisiloxane. This method provides a monochlorosiloxane which can then be used in the preparation of the bis(polyorganosiloxanyl)amine of this invention. The monochlorosiloxanes having various x values can be prepared by allowing the reaction between the monochlorosilane and cyclotrisiloxane to continue over various periods of time and then separating the resulting mixture by using the spinning band distillation technique. The separations can be used to obtain single species or mixtures having the desired x value. A preferred value of x is from 3 to 6 with the most preferred value being 3. U.S. Pat. No. 3,162,662 is hereby incorporated by reference to show the preparation of the monochlorosiloxanes.

The other treating agent component is a silazane as defined by formula (ii) wherein each G is a lower alkyl radical such as methyl, ethyl or propyl; phenyl; or 2-(perfluoroalkyl)ethyl radicals in which each perfluoroalkyl radical has from 1 to 4 inclusive carbon atoms such as trifluoromethyl, perfluoroethyl, or perfluoroisobutyl. Many of these types of silazanes are commercial products. They may be prepared by combining a silane of the formula $G_3SiX$ with ammonia as shown by C. Eaborn cited above. X is a halogen atom, such as chlorine.

The reinforcing silica can be mixed with the treating agent either as a separate step before mixing the silica with polydiorganosiloxane fluid or the treating agent can be added during the mixing of the silica with polydiorganosiloxane fluids. The latter method is the best method as it is more economical.

The reinforcing silica can be treated by vigorously stirring the silica in a closed container with the treating agent. The silica normally has enough water absorbed on its surface to provide the amount necessary for the reaction with the treating agent but additional water may be added in amounts up to about 10 parts by weight of water per 100 parts by weight of silica. Both (i) and (ii) of the treating agent may be added together or they may be added separately, although the results are more uniform when (i) and (ii) are added together. The step of mixing the silica and the treating agent can take place in a closed container as described above or they can be mixed by dispersing the silica first in a solvent non-reactive with the treating agent such as toluene, and then adding the treating agent. After thorough mixing, which is usually accomplished by stirring for 4 to 24 hours, the solvent, if used, ammonia produced by the hydrolysis of the silazane treating agent, and unreacted treating agent are removed by air drying, heating, vacuum, or a combination of such means. An excess of treating agent is preferably used to assure complete treatment of the silica surface as any unreacted treating agent is easily removed in the process. A large excess of treating agent is not harmful as it is removed, however large excesses may be uneconomical. The minimum amount of treating agent of (i) and (ii) is an amount sufficient to provide a ratio of about 5 parts by weight of treating agent per each 100 parts by weight of the finely divided silica.

The optimum amount of treating agent will depend upon the properties desired in a cured silicone elastomer prepared from a treated silica filler and also upon the desired flow properties of the composition in a molding system. The particular optimum range of treating agent can vary because the other components of any given composition may influence the flow properties and the cured elastomer properties. Thus, the user can readily select the amount of treating agent to meet his requirements by using the example found herein as a starting point.

The mole ratio of (i) to (ii) is in the range of from 1:50 to 1:1 and the preferred range is 1:10 to 1:25. The ratio between the components (i) and (ii) to obtain the most desirable physical properties of the final cured silicone elastomer can be determined by simple experimentation since the most desirable ratio is dependent upon the specific ingredients used in the curable silicone elastomer composition for the polydiorganosiloxane fluid, organohydrogensiloxane and platinum catalyst. The examples found herein can be used as a starting point.

The reinforcing silica can also be mixed with the treating agent during the mixing of a silicone elastomer base to produce an in situ treated reinforcing silica. In this process the polydiorganosiloxane fluid is added to a suitable mixer, for instance a dough mixer, and the treating agent is dispersed into the fluid along with water, if water is used. The silica is then added with mixing. After dispersion of the silica in the fluid, the mixture obtained is heated to promote reaction between the silica and the treating agent. A normal heating period would be 1 to 4 hours at a temperature in the range of from 100° to 200° C. Since some silazanes are volatile materials and flammable it is good practice to keep the mixer closed during the mixing procedure with a nitrogen blanket to eliminate oxygen and the danger of fire or explosion. A vacuum on the mixer can be used to draw off unreacted treating agent and other volatile materials in the polydiorganosiloxane fluid. The amount of silazane treating agent [(i)+(ii)] may be varied. The mole ratio of (i) to (ii) for the in situ process is in the same range as described above.

A silicone elastomer base produced in the above manner can be cured to produce a useful silicone elastomer by adding an organoperoxide vulcanizing agent suitable for vulcanizing silicone rubber and then heating the resulting mixture to activate the organoperoxide in a manner well known in the art. These organoperoxide vulcanizing agents include benzylperoxide, 2-4-dichlorobenzoylperoxide, di-tertiary butyl peroxide, 2,5-bis-(tert.-butylperoxy)2,5-dimethylhexane, and dicumyl peroxide.

One of the advantages of the use of the bis(polyorganosiloxanyl)amine (i) of this invention is the greater efficiency or reactivity of the unsaturated group of the short chain polysiloxane portion of the molecule. A smaller amount of the bis(polyorganosiloxanyl)amine produces the same durometer level and modulus level as larger amounts of treating agents containing hexaorganodisilazanes containing the same unsaturated group. This allows the use of smaller amounts of treating agent.

Using the bis(polyorganosiloxanyl)amine in the treating agent also allows the choice of using a comparable ratio of treating agent, but lowering the amount of finely divided silica used in the formulation of silicone elastomer base, thereby lowering the cost and viscosity of the base. Compositions prepared from such bases are suitable for use in low pressure molding systems, such as liquid injection molding processes.

The vinyl-containing polydiorganosiloxane fluids used in this invention are well known in the art. The polydiorganosiloxane fluids have an average of about two silicon-bonded vinyl radicals per molecule, only one vinyl radical is bonded to any one silicon atom, and the remaining organic radicals can be methyl, ethyl, phenyl, or 2-(perfluoroalkyl)ethyl radicals, in which each perfluoroalkyl radical has from 1 to 4 carbon atoms. Examples of the 2-(perfluoroalkyl)ethyl radicals include 3,3,3-trifluoropropyl and 2(perfluoroisobutyl)ethyl. The 2-(perfluoroalkyl)ethyl radicals can be present in an amount of from 0 to 50 inclusive percent and the phenyl radicals can be present in an amount from 0 to 30 percent inclusive, where the percentages are based on the total number of organic radicals in the polydiorganosiloxane fluid. The polydiorganosiloxane fluids are endblocked by triorganosiloxy groups. The triorganosiloxy groups have organic radicals selected from the same group of organic radicals listed above. The preferred polydiorganosiloxane fluids are endblocked by vinyldiorganosiloxy groups, as illustrated by the formula:

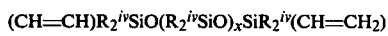

$$(CH=CH)R_2^{iv}SiO(R_2^{iv}SiO)_xSiR_2^{iv}(CH=CH_2)$$

where each $R^{iv}$ is a radical as defined above for the organic radicals and x has a value such that the viscosity is from 0.06 Pa.s up to 200 Pa.s. Preferred silicone elastomer composition are obtained from mixtures of polydiorganosiloxanes with a viscosity ranging from 0.4 Pa.s to 100 Pa.s. The upper portion of this range gives higher tensile properties.

The organohydrogensiloxanes (d) containing silicon-bonded hydrogen atoms are well known in the art such as described by Polmanteer et al. in U.S. Pat. No. 3,697,473 and Lee et al. in U.S. Pat. No. 3,989,668 which patents are hereby incorporated by reference to show examples of organohydrogensiloxanes known in the art. The organohydrogensiloxanes useful in the present invention can be any siloxane having an average of at least 2.1 silicon-bonded hydrogen atoms per molecule and an average of no more than one silicon-bonded hydrogen atom per silicon atom. The remaining valences of the silicon atoms are satisfied by divalent oxygen atoms or by monovalent hydrocarbon radicals having no more than 6 carbon atoms per radical such as methyl, ethyl, or propyl, phenyl, or 2-(perfluoroalkyl)ethyl radicals in which each perfluoroalkyl radical has from 1 to 4 inclusive carbon atoms. The organohydrogensiloxanes can be homopolymers copolymers, and mixtures thereof which contain siloxane units of the following types: $R_2^vSiO$, $R_3^vSiO_{0.5}$, $H(CH_3)SiO$, and $H(CH_3)_2SiO_{0.5}$ where $R^v$ is selected from a group consisting of lower alkyl, phenyl, and 2-(perfluoroalkyl)ethyl radicals. Each perfluoroalkyl radical has from 1 to 4 carbon atoms. Some specific examples of organohydrogensiloxanes include polymethylhydrogensiloxane cyclics, copolymers of trimethylsiloxy and methylhydrogensiloxane units, copolymers of dimethylhydrogensiloxy and methylhydrogensiloxane units, copolymers of trimethylsiloxy, dimethylsiloxane, and methylhydrogensiloxane units and copolymers of dimethylhydrogensiloxy, dimethylsiloxane, and methylhydrogensiloxane units. Preferably the organohydrogensiloxanes have an average of at least 4 silicon-bonded hydrogen atoms per molecule.

Compositions prepared from ingredients (a), (b), (c), and (d) can be cured with the aid of a catalyst (e) which can be any of the platinum-containing catalysts that are known to catalyze the reaction of silicon-bonded hydrogen atoms with silicon-bonded vinyl groups and which are soluble in the polydiorganosiloxane fluid (a). Platinum-containing catalysts which are not soluble in said fluid mixture are not sufficiently effective to satisfactorily cure the compositions. A class of platinum-containing catalysts particularly suitable for use in these compositions are the complexes prepared from chloroplatinic acid as described by Willing in U.S. Pat. No. 3,419,593 which is hereby incorporated by reference to show the complexes and their preparation. One preferred catalyst of this type is a platinum-containing complex which is the reaction product of chloroplatinic acid and sym-divinyltetramethyldisiloxane.

The platinum-containing catalyst (e) can be present in an amount sufficient to provide at least one part by weight of platinum for every one million parts by weight of polydiorganosiloxane fluid (a). It is preferred to use sufficient catalyst (e) so that there is present from 5 to 50 parts by weight platinum for every one million parts by weight of polydiorganosiloxane fluid (a). It is to be understood that amounts of platinum greater than the 50 parts per million are also effective but are unnecessary and wasteful, especially when the preferred catalyst is used.

A mixture of components (a), (d), and (e) may begin to cure immediately on mixing at room temperature, therefore it is necessary to inhibit the action of the catalyst (e) at room temperature with a platinum catalyst inhibitor if the composition is to be stored before molding. Platinum catalyst inhibitors are used to retard the catalytic activity of the platinum at room temperature, but allow the platinum to catalyze the reaction between (a) and (d) at elevated temperature.

One suitable type of platinum catalyst inhibitor is the acetylenic inhibitors described in U.S. Pat. No. 3,445,420 to Kookootsedes et al. which is hereby incorporated by reference to show the acetylenic inhibitors and their use as inhibitors.

A second type of platinum catalyst inhibitor is the olefinic siloxanes that are described in U.S. Pat. No. 3,989,667 to Lee and Marko which is hereby incorporated by reference to show the olefinic siloxanes, their preparation and their use as platinum catalyst inhibitors.

A third type of platinum catalyst inhibitor is a vinylorganocyclosiloxane of the general formula

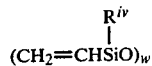

wherein $R^{iv}$ is as defined above and w has an average value of from 3 to 6. Vinylorganocyclosiloxanes are well known in the organosilicon art, especially where $R^{iv}$ is methyl and w is 3, 4, or 5.

The amount of platinum catalyst inhibitor required is simply the amount needed to produce the desired shelf like and yet not extend the cure time of compositions prepared from (a), (b), (c), (d), and (e) to an impractical level. This amount will vary widely and will depend upon the particular inhibitor that is used, the nature and concentration of the platinum-containing catalyst (e) and the nature of the organohydrogensiloxane (d).

Inhibitor added in amounts as small as one mole of inhibitor for every mole of platinum will in some instances cause an inhibition of the catalyst (e) and afford a satisfactory pot life. In other cases, considerably more inhibitor, such as 10, 50, 100, 500 and more moles of inhibitor for every mole of platinum may be needed to achieve the desired combination of pot life and cure time. The exact amount of any particular inhibitor to be used can be determined by simple experimentation. The effect of a platinum catalyst inhibitor can be overcome by heating the inhibited compositions to a temperature of 70° C. or higher.

The amounts of ingredients, (a), (b), (c), and (d) can be varied to achieve a range of properties in the cured elastomer. In general, as more finely divided silica (b) is added, the hardness and tensile strength of the cured product increases. However, the amount of silica filler used should not be so great that the viscosity of the uncured composition becomes too high for practical use in the molding process being used, particularly if the molding process is a low pressure molding system. Compositions of the present invention can be formulated to be used in a liquid injection molding process in which the composition is injected into light weight molds under low pressures, such as 600 kPa cylinder pressure. Such compositions can be cured very rapidly in a hot mold and removed without cooling the mold. The upper viscosity limit of these compositions using reinforcing silica filler is about 160 Pa.s. The amount of reinforcing silica in these compositions can be from 20 to 50 parts by weight based upon 100 parts by weight of polydiorganosiloxane fluid. The preferred range is from 30 to 45 parts.

The amount of (d) should be sufficient to provide enough silicon-bonded hydrogen atoms so that there is from 1 to 5 silicon-bonded hydrogen atoms per vinyl radical wherein the amount of vinyl radical considered is in (a) and (c) combined. A preferred range of silicon-bonded hydrogen atoms to vinyl radical is from 1 to 3.

Compositions of this invention may contain other components that are common to the silicone rubber art, such as pigments, extending filler, antioxidants, compression set additives, and thermal stability additives.

Compositions of this invention are obtained whenever the recited components are mixed together. When the reinforcing silica is mixed with treating agent as a separate step, as discussed above, the treated silica is thereafter mixed with a polydiorganosiloxane fluid to produce a silicone elastomer base. The polydiorganosiloxane fluid, treating agent and reinforcing silica can be mixed together, as also described above, to produce a silicone elastomer base containing an in situ treated silica. In either case the base is then further processed in manners well known in the art to yield a silicone elastomer. Such an elastomer is produced by curing compositions prepared by mixing the required base, organohydrogensiloxane, platinum catalyst, the inhibitor, if the composition is not being molded immediately, and any of the other specialized additives common to the silicone elastomer art, provided they do not interfere with the required cure.

The order of mixing is not critical; however, if the composition is not to be used immediately or if the composition is to be used in a method of liquid injection molding, it is preferred to have inhibitor present when silicone elastomer base, organohydrogensiloxane (d) and catalyst (e) are mixed, since a curing reaction involving these components begins immediately at room temperature if inhibitor is not present.

Since component (d) and the inhibitor frequently are volatile or contain volatile compounds, it is preferred that said components be mixed after heating and/or vacuum operations in the preparation of the bases of this invention have been completed. It is also preferred that no component or mixture of components be heated above 300° C. during the preparation of the compositions of this invention.

It is also possible to prepare a curable silicone elastomer composition of this invention by combining two or more mixtures, each mixture comprising an uncurable combination of some of the components of the compositions. For example, it is within the scope of this invention to prepare a first mixture containing a portion of the silicone elastomer base with the appropriate amount of platinum catalyst (e), and the platinum catalyst inhibitor if desired, and a second mixture containing the remaining silicone elastomer base and the organohydrogen siloxane in the appropriate amount. These two mixtures have an extended shelf life whether a platinum catalyst inhibitor is used or not. When it is desired to cure the composition, the two mixtures are combined and thoroughly mixed. Obviously there are many other ways to combine the recited components to prepare the compositons of this invention in multi-package form.

Compositions of this invention, containing inhibitor are curable by heating them to a temperature sufficient to cause curing, preferably greater than 100° C., either in a confined area or exposed to the atmosphere. Curing temperatures of greater than 300° C. should be avoided. Compositions of this invention are useful in any type of molding operation providing the required temperatures and times to produce the desired degree of cure are available.

The following examples are included for illustrative purposes only, and should not be construed as limiting the invention which is properly delineated by the appended claims. All parts are parts by weight.

EXAMPLE 1

Preparation of

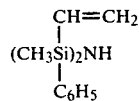

A 5-liter flask was equipped with bubbler, stirrer, and condenser. To the flask, there was added 3 liters of dry hexane and 427 g of methylphenylvinylchlorosilane and thereafter the flask contents were stirred for 10 minutes. Anhydrous ammonia was bubbled through the mixture for one hour, during which the stirring was continued. The resulting mixture contained ammonium chloride which was filtered out using Buchner funnel with a filter paper. The filtrate was collected in a 4-liter vacuum flask. To determine if the reaction was complete anhydrous ammonia was bubbled through a sample of the filtrate and completion was verified by observing that no ammonium chloride was formed. The hexane was removed from the filtrate by vacuum while cooling the flask to maintain a temperature within a range of 0° to 10° C. The residue in the flask was

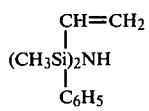

A silicone elastomer base was prepared by mixing 127.5 g of methylphenylvinylsiloxy endblocked polydimethylsiloxane fluid, (1), having a viscosity of approximately 30 Pa.s at 25° C. with 22.5 g of methylphenylvinylsiloxy end-blocked polydimethylsiloxane fluid, (2), having a viscosity of 0.15 Pa.s in a dough mixer. Six grams of water was added and mixing continued for an additional 5 minutes. Then 24 g of hexamethyldisilazane and 1.98 g of the above described dimethyldiphenyldivinyldisilazane were added and mixed for five minutes. To the resulting mixture, 120 g of a finely divided reinforcing silica with a surface area of 400 m$^2$/g was slowly added with mixing over a 0.5 hour period.

The contents of the mixer was then heated to 175° C. and placed under vacuum while mixing continued for about 1 hour, after which, 127.5 g of fluid (1) and 22.5 g fluid (2) were added to the hot mixture and mixing continued for another 0.5 hour. The mixer was then cooled while maintaining the vacuum to yield a silicone elastomer base.

To 90 g of the above silicone elastomer base, there was added with mixing 1.53 g of a trimethylsilyl endblocked polyorganosiloxane crosslinker having an average of 5 methylhydrogensiloxane units and 3 dimethylsiloxane units per molecule, 0.15 g of a platinum catalyst in the form of a chloroplatinic acid complex with symmetrical divinyltetramethyldisiloxane containing about 0.65 percent platinum, and about 0.02 g of 3,5-dimethyl-1-hexyn-3-ol cure inhibitor. The resulting curable silicone elastomer composition was then molded into sheets by pressing and curing for 15 minutes at 175° C. Portions of the sheets were heat aged for 24 hours at 200° C. Physical properties of the sheets were measured in accordance with the procedures of ASTM D412 for tensile and elongation, with ASTM D624 die B for tear and with ASTM D2240 for durometer. The 100% modulus is the tensile stress at 100% strain. The results were as shown in Table I. This is presented for comparative purposes.

EXAMPLE 2

The ingredients, amounts, and process as described in Example 1 were used with the exception that 3.98 g of dimethyldiphenyldivinyldisilazane was used in the manufacture of the base. The amount of polyorganosiloxane crosslinker was increased to 2.118 g so that the ratio of silicon-bonded hydrogen to vinyl remained at the same ratio of 1.75 to 1.0. The test results were as shown in Table I. This is presented for comparative purposes.

EXAMPLE 3

A silicone elastomer base was produced by mixing 170 g of fluid (1) as defined in Example 1 and 30 g of fluid (2) as defined in Example 1 in a dough mixer. Eight grams of water was added and mixing continued for an additional 5 minutes. Then 1.6 g of divinyltetramethyldisilazane and 18 g of hexamethyldisilazane were added and mixed for 5 minutes. To the resulting mixture, 160 grams of the silica as described in Example 1 was added in three equal portions with 5 minutes of mixing between each addition, and another 18 g of hexamethyldisilazane was added. The resulting material was then mixed for 0.5 hour. The contents of the mixer was then heated to 175° C. and placed under vacuum while mixing continued for 1.5 hours. After which 170 g of fluid (1) and 30 g of fluid (2) were added to the hot mixture followed by heating under vacuum with mixing for 0.5 hour. The mixer was then cooled while maintaining the vacuum to yield a silicone elastomer base.

To 40 g of the above silicone elastomer base, there was added with mixing 0.67 g of the polyorganosiloxane crosslinker as described in Example 1, 0.062 g of the platinum catalyst as described in Example 1 and about 0.02 g of the inhibitor of Example 1.

This curable silicone elastomer composition was then molded into a sheet and tested in the manner described in Example 1. The results were as shown in Table 1. This is presented for comparative purposes.

EXAMPLE 4

A silicone elastomer base was produced by mixing 127.5 g of the fluid (1) as described in Example 1, 22.5 g of the fluid (2) as described in Example 1, 2.4 g of divinyltetramethyldisilazane, and 12 g of hexamethyldisilazane in a dough mixer. After mixing these ingredients for 5 minutes, 120 g of the silica as described in Example 1 was added in 3 equal portions with 5 minutes of mixing between each addition. Another 12 g of hexamethyldisilazane was added, and mixed for 5 minutes, then 6 g of water was added and mixed for 0.5 hour. The contents of the mixer was then heated to 175° C., mixed 0.5 hour, vacuum was then applied and mixing was continued for another 0.5 hour. To this hot mixture there was added 127.5 g of fluid (1) and 22.5 g of fluid (2) followed by heating under vacuum for 0.5 hour. The mixer was then cooled while maintaining the vacuum to yield a silicone elastomer base.

To the above silicone elastomer base, there was added ingredients in the amounts and by the procedure as described in Example 3. The results were as shown in Table I. This is presented for comparative purposes.

EXAMPLE 5

Preparation of

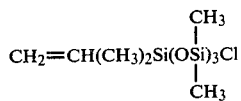

A 3-necked flask was equipped with stirrer, thermometer, and addition funnel. To the flask there was added 666 g (3 moles) of hexamethylcyclotrisiloxane and 209 g of dried acetonitrile. This mixture was heated gently to a temperature in the range of 50°–55° C., 20.9 g of N,N-dimethylacetamide was added, followed by the rapid addition of 442 g (3.5 moles) of dimethylvinylchlorosilane with stirring. The reaction mixture was stirred overnight. After 20 hours, unreacted hexamethylcyclotrisiloxane, excess dimethylvinylchlorosilane and acetonitrile were vacuum stripped from the mixture at room temperature. The remaining material was distilled through a Vigreaux column.

The distillation fractions numbered one through four were combined to give 316 g of product containing 97 percent of a monochlorosiloxane of the formula

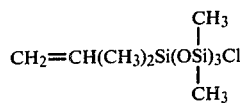

The fifth fraction was approximately 50 g of a product containing 80% of a monochlorosiloxane of the same formula.

Preparation of

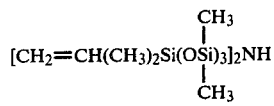

To a 5-liter 3-necked flask, equipped with an air stirrer, condenser, thermometer, and bubbler, there was added 500 ml of distilled

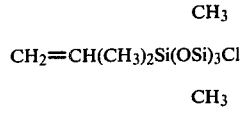

prepared in accordance with the above procedure and three liters of dry hexane. Anhydrous ammonia was rapidly bubbled for two hours through this mixture which was being stirred. A small sample of the mixture was then taken from the flask, the ammonium chloride filtered out and additional ammonia was bubbled through it. Because no ammonium chloride was formed, the reaction was assumed complete. The total mixture was then filtered. The filter cake was washed once with 500 ml of dry hexane. The filtrate was vacuum stripped at 25° C. to remove the hexane.

The resulting product was 97%

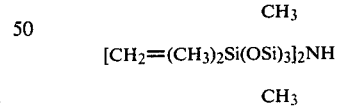

A silicone elastomer base was produced using the ingredients, amounts, and procedure as described in Example 4 with the exception that 4.08 g of the above described

[CH$_2$=(CH$_3$)$_2$Si(OSi)$_3$]$_2$NH with CH$_3$ groups was used in place of the 2.4 g of divinyltetramethyldisilazane.

To 125 g of the above silicone elastomer base, there was added 2.29 g of the polyorganosiloxane crosslinker as described in Example 1, 0.192 g of the platinum catalyst as described in Example 1, and about 0.03 g of the cure inhibitor as described in Example 1.

This curable silicone elastomer composition was molded into a sheet and tested in the manner described in Example 1. The results were as shown in Table 1. The results illustrate the higher durometer and higher modulus obtained with this filler treatment when compared to the results of compositions made using the filler treatment as shown by Examples 1 and 3.

EXAMPLE 6

The ingredients, amounts, and process as described in Example 5 were used with the exception that 8.16 g of

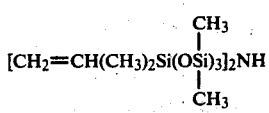

was used in place of the 4.08 g of Example 5 in the manufacture of a silicone elastomer base. The amount of polyorganosiloxane crosslinker was increased to 3.125 g so that the ratio of silicon-bonded hydrogen atoms to vinyl remained the same. The test results were as shown in Table I.

In the above 6 examples the ingredients were identical except for the identity of the silicon-nitrogen compounds containing a reactive vinyl radical. The moles of such silicon-nitrogen compounds have been held to two levels for comparative purposes.

Table I shows that it is possible to obtain higher durometers and/or modulus using lower amounts of bis(-polyorganosiloxanyl)amine. Example 5 showed that one half the amount of bis(polyorganosiloxanyl)amine provided higher durometer and/or modulus compared to otherwise equivalent silazane compositions.

were added and mixed for 5 minutes. Thereafter, 114 g of the silica as described in Example 1 was added in 3 equal portions with 15 minutes mixing between additions. The mixture was mixed for 30 minutes after the last silica addition, then the contents of the mixer were heated to 175° C., vacuum was applied and the mixing was continued for 1 hour. Then, 143.7 g of the fluid (1) and 25.4 g of the fluid (2) were added to the hot mixer followed by mixing for 0.5 hours. The mixer was then cooled while maintaining the vacuum and mixing to yield a silicone elastomer base.

This silicone elastomer base was tested for suitability for use in a low pressure extrusion type molding operation by measuring the weight of base extruded through a 3.175 mm orifice with a pressure of 620 kPa.

| Time Out of Mixer | Grams Extruded Per Minute |
|---|---|
| 16 hours | 85.8 |
| 4 months | 78.0 |
| 6 months | 76.0 |

The above silicone elastomer base was made into a curable silicone elastomer composition by mixing 62.5 g of the base, 1.283 g of a crosslinking mixture consisting of 20% trimethylsilyl endblocked polymethylhydrogensiloxane with a viscosity of approximately 0.03 Pa.s and 80% of the trimethylsilyl endblocked polyor-

TABLE I

| Example | Cmp'd* | Ratio** | Cure | Tensile MPa | Elongation % | 100% Modulus MPa | Tear kN/m | Durometer |
|---|---|---|---|---|---|---|---|---|
| 1 | A | 1/23 | 15 min/175° C. | 7.65 | 595 | 0.96 | 45.5 | 40 |
| 2 | A | 1/11.5 | | 8.16 | 725 | 0.93 | 51.6 | 40 |
| 3 | B | 1/23 | | 9.30 | 550 | 1.41 | 26.2 | 42 |
| 4 | B | 1/11.5 | | 9.80 | 410 | 2.31 | 35.0 | 53 |
| 5 | C | 1/23 | | 9.03 | 472 | 2.07 | 34.1 | 59 |
| 6 | C | 1/11.5 | | 8.06 | 427 | 2.62 | 24.8 | 66 |
| 1 | A | 1/23 | 24 hr/200° C. | 10.06 | 500 | 1.72 | 35.9 | 54 |
| 2 | A | 1/11.5 | | 9.40 | 531 | 1.58 | 34.3 | 53 |
| 3 | B | 1/23 | | 10.09 | 430 | 2.07 | 35.9 | 52 |
| 4 | B | 1/11.5 | | 9.03 | 321 | 3.00 | 26.4 | 60 |
| 5 | C | 1/23 | | 9.59 | 445 | 2.34 | 29.8 | 63 |
| 6 | C | 1/11.5 | | 7.94 | 340 | 3.28 | 10.8 | 72 |

*The letters in this column represent the vinyl silicon-nitrogen compound as follows
A = sym-dimethyldiphenyldivinyldisilazane
B = sym-tetramethyldivinyldisilazane C = [CH$_2$=CH(CH$_3$)$_2$Si(OSi)$_3$]$_2$NH
                           CH$_3$

**Mole Ratio = Moles vinyl silicon-nitrogen compound/moles hexamethyldisilazane

EXAMPLE 7

The silicone elastomer base as described in Example 6 was repeated except that the amount of reinforcing silica was reduced from 40 parts silica per 100 parts of the combined polydimethylsilxoane fluids to 38 parts.

A silicone elastomer base was prepared by mixing in a dough mixer for 5 minutes, 111.3 g of the fluid (1) as described in Example 1 with 19.6 g of the fluid (2) as described in Example 1 and 6.0 g of water. Then 24 g of hexamethyldisilazane and 8.16 g of

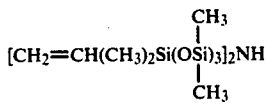

ganosiloxane crosslinker as described in Example 1, 0.096 g of the platinum catalyst as described in Example 1, and 0.01 g of the cure inhibitor as described in Example 1.

This curable silicone elastomer composition was then molded and tested in the manner described in Example 1. The results were as follows:

| Tensile, MPa | 7.75 |
|---|---|
| Elongation, % | 370.00 |
| 100% Modulus, MPa | 2.76 |
| Tear, kN/m | 34.6 |
| Durometer | 61 |

That which is claimed is:
1. A bis(polyorganosiloxanyl)amine of the formula

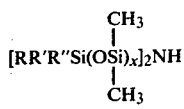

[RR'R"Si(OSi)$_x$]$_2$NH where R is methyl, ethyl, or phenyl; R' is methyl or ethyl, R" is vinyl or allyl; and x is an integer of from 2 to 12 inclusive.

2. The bis(polyorganosiloxanyl)amine according to claim 1 wherein R is methyl; R' is methyl; and R" is vinyl.

3. The bis(polyorganosiloxanyl)amine according to claim 2 wherein x is 3.

4. A silicone elastomer base comprising a product obtained by mixing (a) 100 parts by weight of triorganosiloxy endblocked polydiorganosiloxane fluid wherein each organic radical is selected from a group consisting of methyl, ethyl, vinyl, phenyl and 2-(perfluoroalkyl)ethyl radicals in which each perfluoroalkyl radical has from 1 to 4 inclusive carbon atoms, there being an average of about 2 vinyl radicals per molecule and only one vinyl radical bonded to any one silicon atom, there being from 0 to 50 inclusive percent 2-(perfluoroalkyl)ethyl radicals, and from 0 to 30 inclusive percent phenyl radicals, both being based on the total number of organic radicals in the polysiloxane fluid; the fluid having a viscosity from 0.4 Pa.s to 100 Pa.s; (b) from 20 to 50 parts by weight of a finely divided silica with a surface area of at least 50 square meters per gram; (c) a treating agent consisting essentially of (i) the bis(polyorganosiloxanyl)amine of claim 1 and (ii) a silazane of the formula (G$_3$Si)$_2$)NH wherein each G is selected from a group consisting of lower alkyl, phenyl, and 2-(perfluoroalkyl)ethyl radicals in which each perfluoroalkyl radical has from 1 to 4 inclusive carbon atoms; (c) being present in an amount sufficient to provide a ratio of at least 5 parts by weight of the treating agent mixture per 100 parts by weight of the finely divided silica (b); the treating agent having a mole ratio of (i) to (ii) of from 1/50 to 1/1.

5. A process for producing a silicone elastomer comprising (I) mixing silicone elastomer base of claim 4 and a platinum catalyst which is soluble in the polydiorganosiloxane fluid of the silicone elastomer base and there being sufficient platinum catalyst to provide at least 1 part by weight of platinum per one million parts by weight of polysiloxane fluid (a) to produce a mixture (A), (II) mixing silicone elastomer base of claim 4 and an organohydrogen siloxane to produce a mixture (B), said organohydrogensiloxane having an average of at least 2.1 silicon-bonded hydrogen atoms per molecule, said organohydrogensiloxane consisting essentially of siloxane units selected from a group consisting of H(CH$_3$)SiO units, R$_2^v$SiO units, H(CH$_3$)$_2$SiO$_{0.5}$ units, and R$_3^v$SiO$_{0.5}$ units, R$^v$ being selected from a group consisting of lower alkyl, phenyl, and 2-(perfluoroalkyl)ethyl radicals in which each perfluoroalkyl radical has from 1 to 4 inclusive carbon atoms, the organohydrogensiloxane being present in an amount sufficient to provide from 1 to 5 inclusive silicon-bonded hydrogen atoms per vinyl radical wherein the vinyl radical is the combined amount in mixture (A) and mixture (B), (III) mixing mixture (A) and mixture (B), and thereafter (IV) allowing an elastomer to form.

6. A process for preparing a silicone elastomer base containing an in situ treated silica comprising (I) mixing (a) 100 parts by weight of triorganosiloxy endblocked polydiorganosiloxane fluid wherein each organic radical is selected from a group consisting of methyl, ethyl, vinyl, phenyl, and 2-(perfluoroalkyl)ethyl radicals in which each perfluoroalkyl radical has from 1 to 4 inclusive carbon atoms, there being an average of about 2 vinyl radicals per molecule and only one vinyl radical bonded to any one silicon atom, there being from 0 to 50 inclusive percent 2-(perfluoroalkyl)ethyl radicals and from 0 to 30 inclusive percent phenyl radicals, both being based on the total number of organic radicals in the polysiloxane fluid; the fluid having a viscosity of from 0.4 Pa.s to 100 Pa.s, (b) from 20 to 50 parts by weight of a finely divided silica with a surface area of at least 50 square meters per gram, (c) a treating agent consisting essentially of (i) the bis(polyorganosiloxanyl)amine of claim 1, and (ii) a silazane of the formula (G$_3$Si)$_2$NH where each G is selected from a group consisting of lower alkyl, phenyl and 2-(perfluoroalkyl)ethyl radicals in which each perfluoroalkyl radical has from 1 to 4 inclusive carbon atoms, the treating agent being present in an amount sufficient to provide at least 5 parts by weight of the treating agent for each 100 parts by weight of the finely divided silica (b); the treating agent having a mole ratio of (i) to (ii) of from 1/50 to 1/1, (II) heating a resulting material of step (I) at a temperature above 100° C. for from about 1 to 4 hours using a volatile removal means, (III) cooling a material of step (II) to obtain a silicone elastomer base.

7. The process in accordance with claim 6 in which there is mixed with the resulting silicone elastomer base, an organohydrogen siloxane having an average of at least 2.1 silicon-bonded hydrogen atoms per molecule, said organohydrogen siloxane consisting essentially of units selected from a group consisting of H(CH$_3$)SiO units, R$_2^v$SiO units, H(CH$_3$)$_2$SiO$_{0.5}$ units, and R$_3^v$SiO$_{0.5}$ units, in which R$^v$ is selected from a group consisting of lower alkyl, phenyl, and 2-(perfluoroalkyl)ethyl radicals in which each perfluoroalkyl radical has from 1 to 4 inclusive carbon atoms, the amount of organohydrogensiloxane being sufficient to provide from 1 to 5 inclusive silicon-bonded hydrogen atoms per vinyl radical in the silicone elastomer base; a platinum catalyst soluble in the polydiorganosiloxane fluid (a) and there being sufficient platinum catalyst to provide at least 1 part by weight of platinum per one million parts by weight of polydiorganosiloxane fluid (a), and an amount of a platinum catalyst inhibitor sufficient to extend the shelf life at ambient temperatures.

8. The composition produced by the process of claim 7.

9. A cured silicone elastomer produced by heating the compositions of claim 8 to a temperature sufficiently high to inactivate the platinum catalyst inhibitor and cause curing of the composition.

10. A cured silicone elastomer produced by the process of claim 5.

UNITED STATES PATENT AND TRADEMARK OFFICE
CERTIFICATE OF CORRECTION

PATENT NO. : 4,152,315

DATED : May 1, 1979

INVENTOR(S) : Chi-long Lee and Myron T. Maxson

It is certified that error appears in the above—identified patent and that said Letters Patent is hereby corrected as shown below:

Abstract - the word "pinely" should read "finely"

Column 3, the first formula should read --

(i) $[RR'R''Si(OSi)_x]_2NH$ with $CH_3$ substituents 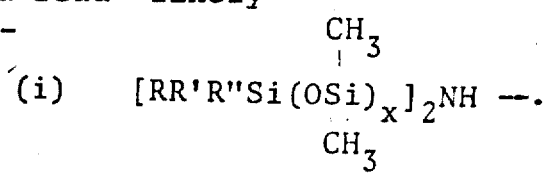

Column 3, the second formula should read -- (ii) $(G_3Si)_2NH$ 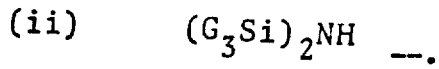

Column 5, line 66 - the word "agents" should read "agent"

Column 5, line 56 - the word "benzylperoxide" should read "benzoylperoxide"

Column 12, lines 38-43 - the formula "$[CH_2=(CH_3)_2Si(OSi)_3]_2NH$" with $CH_3$ substituents should read "$[CH_2=CH(CH_3)_2Si(OSi)_3]_2NH$" with $CH_3$ substituents

UNITED STATES PATENT AND TRADEMARK OFFICE
CERTIFICATE OF CORRECTION

PATENT NO. : 4,152,315

DATED : May 1, 1979

INVENTOR(S) : Ch-long Lee and Myron T. Maxson

It is certified that error appears in the above—identified patent and that said Letters Patent is hereby corrected as shown below:

Column 12, lines 48-54 - the formula "$[CH_2=(CH_3)_2Si(OSi)\substack{CH_3\\3\\CH_3}]_2NH$"

should read "$[CH_2=CH(CH_3)_2Si(OSi)\substack{CH_3\\3\\CH_3}]_2NH$"

Signed and Sealed this

First Day of June 1982

[SEAL]

Attest:

GERALD J. MOSSINGHOFF

Attesting Officer

Commissioner of Patents and Trademarks